US008895077B2

(12) United States Patent
Perl et al.

(10) Patent No.: US 8,895,077 B2
(45) Date of Patent: Nov. 25, 2014

(54) METHODS FOR PREVENTING OR TREATING INFECTIOUS DISEASES CAUSED BY EXTRACELLULAR MICROORGANISMS, INCLUDING ANTIMICROBIAL-RESISTANT STRAINS THEREOF, USING GALLIUM COMPOUNDS

(75) Inventors: Daniel P. Perl, Dobbs Ferry, NY (US); Sharon Moalem, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 12/058,484

(22) Filed: Mar. 28, 2008

(65) Prior Publication Data
US 2008/0241275 A1    Oct. 2, 2008

Related U.S. Application Data

(60) Provisional application No. 60/909,658, filed on Apr. 2, 2007.

(51) Int. Cl.
A61K 33/24        (2006.01)
A61K 31/28        (2006.01)
A61K 31/5375      (2006.01)
A61K 38/14        (2006.01)
A61P 31/04        (2006.01)

(52) U.S. Cl.
CPC ............... A61K 33/24 (2013.01); A61K 31/28 (2013.01); Y10S 424/06 (2013.01)
USPC .... 424/650; 424/DIG. 6; 514/3.1; 514/231.2; 514/238.8; 514/492

(58) Field of Classification Search
None
See application file for complete search history.

(56) References Cited

U.S. PATENT DOCUMENTS

| 5,229,418 | A | 7/1993 | Collington et al. |
| 5,258,376 | A | 11/1993 | Bernstein |
| 5,358,705 | A | 10/1994 | Boggs et al. |
| 5,556,645 | A | 9/1996 | Bockman et al. |
| 5,574,027 | A | 11/1996 | Bernstein |
| 5,679,377 | A | 10/1997 | Bernstein et al. |
| 5,747,482 | A | 5/1998 | Bernstein |
| 5,843,936 | A | 12/1998 | Bernstein |
| 5,883,088 | A | 3/1999 | Bernstein |
| 5,916,885 | A | 6/1999 | Bernstein |
| 5,968,922 | A | 10/1999 | Bernstein |
| 5,981,518 | A | 11/1999 | Bernstein |
| 5,997,912 | A | 12/1999 | Schlesinger et al. |
| 5,998,397 | A | 12/1999 | Bernstein |
| 6,004,951 | A | 12/1999 | Bernstein |
| 6,048,851 | A | 4/2000 | Bernstein |
| 6,087,354 | A | 7/2000 | Bernstein |
| 6,203,822 | B1 | 3/2001 | Schlesinger et al. |
| 6,221,350 | B1 | 4/2001 | Brown et al. |
| 6,287,606 | B1 | 9/2001 | Bockman et al. |
| 6,297,242 | B1 | 10/2001 | Hlasta |
| 6,506,413 | B1 | 1/2003 | Ramaekers |
| 2004/0038956 | A1 | 2/2004 | Nakada et al. |
| 2004/0087015 | A1 | 5/2004 | Vournakis et al. |
| 2005/0220895 | A1 | 10/2005 | Bucalo et al. |
| 2006/0018945 | A1 | 1/2006 | Britigan et al. |
| 2007/0231406 | A1* | 10/2007 | Bucalo et al. ............... 424/617 |

FOREIGN PATENT DOCUMENTS

| WO | WO 9619220 A1 * | 6/1996 |
| WO | WO-98/30102 A1 | 7/1998 |
| WO | WO-03/053347 A2 | 7/2003 |
| WO | WO 2007/053581 | 5/2007 |
| WO | WO-2007/053581 A2 | 5/2007 |
| WO | WO 2008/036787 A1 | 3/2008 |
| WO | WO 2009/009171 | 1/2009 |

OTHER PUBLICATIONS

Bland et al., Antimicrobial Agents and Chemotherapy (2004), vol. 48, No. 6, 1983-1988.*
Arnold et al., Veterinary Microbiology (2012), vol. 155, pp. 389-394.*
L. Bernstein, "Mechanisms of Therapeutic Activity for Gallium", Pharmacological Reviews, vol. 50, No. 4, pp. 665-682 (1998).
G. Eby, "Is Navicular Disease in Horses Curable with Gallium Nitrate? Yes, if treatment is started sufficiently early—lameness controlled in serious cases", http://www.coldcure.com/html/nav.html, pp. 1-27 (rev. Oct. 15, 2005).
D. H. Howard, "Acquisition, Transport, and Storage of Iron by Pathogenic Fungi", Clinical Microbiology Reviews, vol. 12, No. 3, pp. 394-404 (1999).
O. Olakanmi, et al., "Gallium Disrupts Iron Metabolism of Mycobateria Residing within Human Macrophages", Infection and Immunity, vol. 68, No. 10, pp. 5619-5627 (Oct. 2000).
E. D. Weinberg, "The Lactobacillus Anomaly: Total Iron Abstinence", Perspectives in Biology and Medicine, vol. 40, No. 4, pp. 578-583 (1997).
C. M. Litwin, et al., "Role of Iron in Regulation of Virulence Genes", Clinical Microbiology Reviews, vol. 6, No. 2, pp. 137-149 (Apr. 1993).
G. Spatafora, et al., "Expression of Streptococcus mutans fimA is iron-responsive and regulated by a DtxR homologue", Microbiology, vol. 147, pp. 1599-1610 (2001).

(Continued)

Primary Examiner — Abigail Fisher
Assistant Examiner — Frank Choi
(74) Attorney, Agent, or Firm — JMB Davis Ben-David

(57) ABSTRACT

The present invention relates to methods for preventing or treating infectious diseases caused by extracellular microorganisms, such as bacteria and fungi, by systemically administering to a patient a compound containing gallium. The extracellular microorganisms targeted by the present methods include methicillin-resistant *Staphylococcus aureus* (MRSA), vancomycin-resistant *Enterococcus faecalis* (VRE), *E. coli* O157:H7, fluoroquinolone-resistant *Salmonella typhi*, and the like. Furthermore, in the present methods, gallium compounds can be co-administered with one or more conventional antimicrobial agents to treat infectious diseases with reduced risks of creating multi-drug resistant pathogens. The methods of the present invention is also applicable to those microorganisms, such as ulcer-causing *Helicobacter pylori*, complete eradication of which so far has been difficult to achieve.

5 Claims, No Drawings

(56) References Cited

OTHER PUBLICATIONS

D. R. Richardson, "Cytotoxic Analogs of the Iron(III) Chelator Pyridoxal Isonicotinoyl Hydrazone: Effects of Complexation with Copper(II), Gallium(III), and Iron (III) on Their Antiproliferatives Activities", Antimicrobial Agents and Chemotherapy, vol. 41, No. 9, pp. 2061-2063 (Sep. 1997).
J. D.B. Featherstone, "The Science and Practice of Caries Prevention", JADA, vol. 131, pp. 887-899 (Jul. 2000).
S.L. Evans, et al., "Ferrous Iron Transport in *Streptococcus mutans*", Journal of Bacteriology, vol. 168, No. 3, pp. 1096-1099 (Dec. 1986).
P. Heymann, et al., "The Siderophore Iron Transporter of *Candida albicans* (Sit1p/Arn1p) Mediates Uptake of Ferrichrome-Type Siderophores and is Required for Epithelial Invasion", Infection and Immunity, vol. 70, No. 9, pp. 5246-5255 (Sep. 2002).
F. Archibald, "*Lactobacillus plantarum*, an organism not requiring iron", FEMS Microbiology Letters, vol. 19, pp. 29-32 (1983).
R. H. Adamson, et al., "Studies on the Antitumor Activity of Gallium Nitrate (NSC-15200) and Other Group IIIa Metal Salts", Cancer Chemotherapy Reports, Part I, vol. 59, No. 3, pp. 599-610 (May/Jun. 1975).
B. J. Foster, et al., "Gallium Nitrate: The Second Metal with Clinical Activity", Cancer Treatment Reports, vol. 70, No. 11, pp. 1311-1319 (Nov. 1986).
C. R. Chitambar, et al., "Evaluation of Continuous-Infusion Gallium Nitrate and Hydroxyurea in Combination for the Treatment of Refractory Non-Hogkin's Lymphoma", Am, J. Clin. Oncol. (CCT), vol. 20, No. 2, pp. 173-178 (1997).
R. P. Warrell, Jr., et al., "Gallium in the Treatment of Hypercalcemia and Bone Metastasis 12", Important Advances in Oncology, pp. 205-220 (1989).
R. S. Bockman, et al., "Treatment of Patients with Advanced Paget's Disease of Bone with Two Cycles of Gallium Nitrate", Seminars in Arthritis and Rheumatism, vol. 23, No. 4, pp. 268-269 (Feb. 1994).
R. P. Warrell, "Gallium Nitrate Inhibits Calcium Resorption from Bone and Is Effective Treatment for Cancer-related Hypercalcemia", J. Clin. Invest., vol. 73, pp. 1487-1490 (May 1984).
V. Matkovic, et al., "Gallium Prevents Adjuvant Arthritis in Rats and Interferes with Macrophage/T-Cell Function in the Immune Response", Current Therapeutic Research, vol. 50, No. 2, pp. 255-267 (Aug. 1991).
C. Whitacre, et al., "Suppression of experimental autoimmune encephalomyelitis by gallium nitrate", Journal of Neuroimmunology, vol. 39, pp. 175-182 (1992).
C. G. Orosz, et al., "Prevention of Murine Cardiac Allograft Rejection with Gallium Nitrate", Transplantation, vol. 61, No. 5, pp. 783-791 (Mar. 1996).
M. C. Lobanoff, et al., "Effect of Gallium Nitrate on Experimental Autoimmune Uveitis", Exp. Eye Res., vol. 65, pp. 797-801 (1997).
C. Levaditi, et al., "Le gallium, proprietes therapeutiques dans la syphilis et les trypanosomiases experimentales", Academie des Sciences, pp. 1142-1143 (May 1931).
O. Olakanmi, et al., "Gallium inhibits growth of pathogenic mycobacteria in human macrophages by disruption of bacterial iron metabolism: a new therapy for tuberculosis and mycobacterium avium complex?" J. of Investigative Medicine, No. 3, p. 234A (Apr. 1997).
B. R. Byers, et al., "Microbial Iron Transport: Iron Acquisition by Pathogenic Microorganisms", Metal Ions in Biological Systems, vol. 35, pp. 37-66 (1998).
M. L. Guerinot, "Microbial Iron Transport", Annu. Rev. Microbiol., vol. 48, pp. 743-772 (1994).
R. D. Shannon, "Revised Effects Ionic Radii and Systematic Studies of Interatomic Distances in Halides and Chalcogenides", Acta Cryst., vol. A32, pp. 751-767 (1976).
Huheey, et al., "Inorganic Chemistry: Principles of Structure and Reactivity", 4th Edition, Harper Collins College Publishers (1993).
D. Hancock, "Parametric Correlation of Formation Constants in Aqueous Solution. 2. Ligands with Large Donor Atoms", Inorg. Chem., vol. 19, pp. 2709-2714 (1980).

J. Clausen, "67Ga Binding to Human Serum Proteins and Tumor Components", Cancer Research vol. 34, pp. 1931-1937 (Aug. 1974).
S. Vallabhajosula, "Radiogallium Localization in Tumors: Blood Binding and Transport and the Role of Transferrin", J. Nucl Med, vol. 21, No. 7, pp. 650-656 (1980).
J. E. Posey, et al., "Lack of a Role for Iron in the Lyme Disease Pathogen", Science, vol. 288, pp. 1651-1653 (Jun. 2000).
E. D. Weinberg, "Iron and Infection", Microbiological Reviews, vol. 42, No. 1, pp. 45-66 (Mar. 1978).
J. B. Neilands, "Evolution of Biological Iron Binding Centers", Struc. Bond, vol. 11. pp. 145-170 (1972).
T. G. Spiro, "The Hydrolytic Polymerization of Iron(III)", J. of American Chemical Society, vol. 88, No. 12 pp. 2721-2726 (Jun. 1966).
D. Van Der Helm, et al., "Hydroxamates and Polycarboxylates as Iron Transport Agents (Siderophores) in Fungi", Metal Ions in Fungi, vol. 11, pp. 39-98 (1994).
J. H. Crosa, "Signal Transduction and Transcriptional and Post-transcriptional Control of Iron-Regulated Genes in Bacteria", Microbiology and Molecular Biology Reviews, vol. 61, No. 3, pp. 319-336 (Sep. 1997).
S. M. Payne, "Detection, Isolation and Characterization of Siderophores", Methods in Enzymology, vol. 235, pp. 329-344 (1994).
C. R. Chitambar, et al., "Uptake of Gallium-67 by Human Leukemic Cells: Demonstration of Transferrin Receptor-dependent and Transferrin-independent Mechanisms", Cancer Research, vol. 47, pp. 3939-3934 (Aug. 1987).
P. A. Todd, et al., "Gallium Nitrate—A Review of its Pharmacological Properties and Therapeutic Potential in Cancer-Related Hypercalcaemia", Drugs, vol. 42, No. 2, pp. 261-273 (1991).
A. R. Jonkhoff, et al., "Gallium-67 radiotoxicity in human U937 lymphoma cells". Br. J. Cancer, vol. 67, pp. 693-700 (1993).
D.M. Winn, et al., "Coronal and Root Caries in the Dentition of Adults in the United States, 1988-1991", J. Dent. Res., vol. 75 (Special Issue), pp. 642-651 (Feb. 1996).
Jarvis, Lisa M., "An Uphill Battle: With short lives and uncertain profits, antibiotics are a unique development challenge for drug companies", Chemical & Engineering News, pp. 15-20 (Apr. 14, 2008).
Jarvis, Lisa M., "Imminent Threat: As gram-negative bacteria become resistant to current antibiotics, the search for new drugs accelerates", Chemical & Engineering News, pp. 22-24 (Apr. 14, 2008).
Jarvis, Lisa M., "Communal Living: Scientists across academia and industry are making a concerted effort to understand and control bacteria that form biofilms", Chemical & Engineering News, pp. 15-23 (Jun. 9, 2008).
"Ordering - EBY'S Gallium Nitrate Mineral Water 14% Concentrate", http://web.archive.org/web/20041015084724/coldcure.com/html/galliumsales.html, (version Oct. 12, 2004).
"Eby's Gallium Mineral Water 14% Concentrate" Bottle Label, from http://web.archive.org/web/20050521015839/coldcure.com/gif/galliumlabelconcentrate.gif, (version Oct. 12, 2004).
Stojiljkovic et al., "Non-iron metalloporphyrins: potent antibacterial compounds that exploit haem/Hb uptake systems of pathogenic bacteria", Molecular Microbiology, vol. 31, No. 2, pp. 429-442 (1999).
Mar. 16, 2010 Supplementary European Search Report from related European Patent Application No. 08826313.2.
Pulz, Matthias et al., "Comparison of a Shiga Toxin Enzyme-Linked Immunbsorbent Assay and Two Types of PCR for Detection of Shiga Toxin-Producing *Escherichia coli* in Human Stool Specimens", J. Clinical Microbiology, 41(10):4671-4675 (Oct. 2003).
Gerrish, Robert S. et al., "PCR versus Hybridization for Detecting Virulence Genes of Enterohemorrhagic *Escherichia coil*", Emerging Infectious Diseases, 13(8):1253-55 (Aug. 2007).
Cleary, Thomas G., "The Role of Shiga-Toxin-Producing *Escherichia coli* in Hemorrhagic Colitis and Hemolytic Uremic Syndrome", Semin. Pediatr. Infect. Dis., 15:260-265 (2004).
Tarr, Phillip I., et al., "Shiga-toxin-producing *Escherichia coli* and haemolytic uraemic syndrome", The Lancet, 365:1073-86 (Mar. 2005).

(56) References Cited

OTHER PUBLICATIONS

Oughton, Matthew T. et al., "Acute Infectious Diarrhea", In: Rakel & Bope: Conn's Current Therapy, Philadelphia: Saunders Elsevier (2008).
Lee, A. et al., "A Standardized Mouse Model of *Helicobacter pylori* Infection: Introducing the Sydney Strain", Gastroenterology 112:1386-97 (1997).
Collery, et al., "Gallium in cancer treatment", Critical Reviews in Oncology/Hematology 42:283-296 (2002).
Sellers, L.J., "Big Pharma Bails on Anti-Infectives Research", Pharmaceutical Executive 23(12):22 (Dec. 2003).
Keenan, J.I. et al., "The effect of *Helicobacter pylori* infection and dietary iron deficiency on host iron homeostasis: A study in mice", Helicobacter 9(6):643-650 (2004).
Knobloch, K.-M. et al., "Biofilm formation is not necessary for development of quinolone-resistant "persister" cells in an attached *Staphylococcus epidermidis* polulation", Int'l Jour. of Artificial Organs 31(9):752-759 (2008).
Arias, Cesar. A. et al., "Antibiotic-Resistant Bugs in the 21st Century—A Clinical Super-Challenge", N. Engl. J. Med. 360(5): 439-443 (Jan. 29, 2009).
Boucher, Helen W. et al., "Bad Bugs, No Drugs: No ESKAPE! An Update from the Infectious Diseases Society of America", CID 48:1-12 (Jan. 2009).
Foucault, Cedric & Brouqui, Philippe, "How to fight antimicrobial resistance", FEMS Immunol. Med. Microbiol. 49:173-183 (2007).
Kristian, Sascha A. et al., "The ability of biofilm formation does not influence virulence of *Staphylococcus aureus* and host response in a mouse tissue cage infection model", Microbial Pathogenesis 36:237-245 (2004).
Lynch, A. Simon and Robertson, Gregory T., "Bacterial and Fungal Biofilm Infections", Annu. Rev. Med. 59:415-28 (2008).
Metlay, Joshua P. et al., "Antimicrobial Drug Resistance, Regulation, and Research", Emerging Infectious Diseases 12(2):183-190 (Feb. 2006).
O'Neill, Eoghan et al., "Association between Methicillin Susceptibility and Biofilm Regulation in *Staphylococcus aureus* Isolates from Device-Related Infections", J. Clin. Micro. 45(5):1379-1388 (May 2007).
Ramadhan, A.A. and Hegedus, E., "Biofilm formation and esp gene carriage in *Enterococci*", J. Clin. Pathol. 58:685-686 (2005).
Smith, Karen et al., "Comparison of biofilm-associated cell survival following in vitro exposure of meticillin-resistant *Staphylococcus aureus* biofilms to the antibiotics clindamycin, daptomycin, linezolid, tigecycline and vancomycin", Int. J. Antimicrob. Agents (2008), doi:10.1016/j.ijantimicag.2008.08.029.
Stewart, Philip S., "Mechanisms of antibiotic resistance in bacterial biofilms", Int. J. Med. Microbiol. 292:107-113 (2002).
Hubbard, Julia A.M. et al., "Effects of iron-limitation of *Escherichia coli* on growth, the respiratory chains and gallium uptake", Arch. Microbiol. 146:80-86 (1986).
Bajpai, K.K. et al., "Anti-fungal activities of diorgano gallium, indium and thallium diethyldithiocarbamates", Indian Phytopathology 29:335-337 (1976).
Abu-Dari, Kamar, et al., "Antimicrobial Activity of Thiohydroxamic Acids and their Metal Complexes : II. The Synthesis and Antimicrobial Activity of N-Methylthioacetohydroxamic Acid and its Zn, Cu, Fe and Ga Complexes", Dirasat (Pure and Applied Sciences) 208(2): 7-16 (1993).
Srivastava, T.N. et al., "Anti-microbial activities of diaryl gallium, indium and thallium compounds", Indian J. Agric. Sci. 43(1) 88-93 (Jan. 1973).
Al-Aoukaty, Ala et al., "Gallium toxicity and adaptation in *Pseudomonas fluorescene*", FEMS Microbiology Letters 92:265-272 (1992).
Gascoyne, D.J. et al., "Capacity of siderophore—producing alkalophilic bacteria to accumulate iron, gallium and aluminium", Appl. Micro. Biotechnol. 36:136-141 (1991).
Wagner, S. et al., "Bismuth subsalicylate in the treatment of H2 blocker resistant duodenal ulcers: role of *Helicobacter pylori*", Gut 33:179-183 (1992).
"Innovation or Stagnation—Challenge and Opportunity on the Critical Path to New Medical Products", FDA U.S. Department of Health and Human Services (Mar. 2004).
"Bad Bugs, No Drugs—As Antibiotic Discovery Stagnates . . . A Public Health Crisis Brews", Infectious Diseases Society of America (Jul. 2004).
Harrison, P.F., Lederberg, J., "Antimicrobial Resistance: Issues and Options", National Academy Press (1998).
Jan. 22, 2009 International Search Report and the Written Opinion of the International Search Authority from related PCT Application No. PCT/US2008/058666.
Oct. 24, 2008 International Search Report and the Written Opinion of the International Search Authority from related PCT Application No. PCT/US2006/042381.
European Search Report dated Oct. 24, 2012 for corresponding application EP 12 17 5823.
Louis B. Rice, MD, "Antimicrobial Resistance in Gram-Positive Bacteria", The American Journal of Medicine, vol. 119, No. 6A, pp. S11-S19 (Jun. 2006).
P. S. Stewart, and J.W. Costerton, "Antibiotic Resistance of Bacteria in Biofilms", The Lancet, vol. 358, pp. 135-138 (Jul. 14, 2001).
Timothy J. Foster, "The *Staphylococcus aureus* Superbug", The Journal of Clinical Investigation, vol. 114, No. 12, pp. 1693-1695 (Dec. 2004).
H. Lode, "Management of serious nosocomial bacterial infections: do current therapeutic options meet the need?," European Society of Clinical Microbiology and Infectious Diseases, vol. 11, pp. 778-787 (Oct. 2005).
Andrew Pollack, "Antibiotics Research Subsidies Weighted by U.S.", New York Times, Nov. 5, 2010.
Nicholas D. Kristoff, "The Spread of Superbugs", New York Times, Mar. 7, 2010.
Emery; 1986; Exchange of Iron by Gallium in Siderophores; Biochemistry 1986, 25, 4629-4633.

\* cited by examiner

METHODS FOR PREVENTING OR TREATING INFECTIOUS DISEASES CAUSED BY EXTRACELLULAR MICROORGANISMS, INCLUDING ANTIMICROBIAL-RESISTANT STRAINS THEREOF, USING GALLIUM COMPOUNDS

1. INTRODUCTION

This is a utility application claiming the benefit, under 35 U.S.C. §119(e), of U.S. Provisional Application No. 60/909,658, filed Apr. 2, 2007, the entirety of which is incorporated herein by reference.

The present invention relates to methods of preventing or treating infectious diseases caused by various extracellular microorganisms, including bacteria and fungi, using gallium compounds. In particular, the invention relates to the pharmaceutical use of gallium compounds in preventing or treating infectious diseases by systemic administration thereof, such as oral administration, intravenous administration, intramuscular administration, subcutaneous administration, and the like. Infectious diseases that are preventable or treatable by the present invention include those caused by microorganisms that are known to be resistant to conventional antibiotics and/or drugs.

2. BACKGROUND OF THE INVENTION

The emergence of an increasing number of deadly pathogenic microorganisms that are resistant to conventional antibiotics and other antimicrobial agents has become a great concern to public health worldwide. The over-prescription/over-use of antibiotics in humans and farm animals has contributed to a rapid development of antibiotics-resistant strains of various microorganisms. For example, *Staphylococcus aureus*, known to be a common cause of hospital-acquired ("nosocomial") infections that can spread to the heart, bones, lungs, and bloodstream with fatal consequences if not treated, was well controlled by penicillin in the early 1940s. However, by the late 1960s, more than 80 percent of *Staphylococcus aureus* had developed resistance against penicillin and, by 1972, 2 percent of *Staphylococcus aureus* were found to be methicillin-resistant. The percentage of methicillin-resistant bacteria continued to rise to 57.1 percent by 2002 ("Bad Bugs, No Drugs" by Infectious Diseases Society of America ("IDSA"), July 2004, based on Centers for Disease Control ("CDC") National Nosocomial Infections Surveillance System, August 2003).

Similarly, the percentage of enterococci, an important cause of endocarditis, as well as other nosocomial infections, including urinary tract and wound infections and bacteremia, that are resistant to vancomycin (VRE) has increased since the late 1980s and, in 2002, more than 27 percent of the tested enterococci samples from intensive care units were resistant to vancomycin (by IDSA, 2004, supra). Other bacteria known to have developed antibiotics resistance include methicillin resistant, coagulase-negative staphylococci ("CNS"), ceftazidime resistant *Pseudomonas aeruginosa*, amipicillin resistant *Escherichia coli*, ceftazidime resistant *Klebsiella pneumoniae*, penicillin resistant *Streptococcus pneumoniae*, and the like. In addition, drug-resistance is no longer limited to hospital-acquired infections, but has spread to community-acquired infections, as evidenced by, for example, a total of 12,000 cases of community-acquired methicillin-resistant *Staphylococcus aureus* (MRSA) infections found in correctional facilities in Georgia, Calif., and Texas between 2001 and 2003 (2004, IDSA, supra).

Antibiotic-resistant microorganisms cause an enormous economic burden to society. Infectious diseases caused by drug-resistant microorganisms require longer hospitalizations, higher costs for alternative medications, more lost work days and so forth, and often result in death. According to the report by the Institute of Medicine ("IOM") (1998, *Antimicrobial Resistance: Issues and Options*), infections caused by MRSA cost an average of $31,400 per case to treat. The total cost to U.S. society of drug-resistant microorganisms is said to be at least $4 billion to $5 billion annually.

Despite the urgent need for new drugs to control antimicrobial resistance, development of new antibiotics has slowed considerably in recent years as the focus of product development in the pharmaceutical fields has increasingly shifted toward chronic diseases, rather than to acute illness, such as acute bacterial infections, mainly due to higher profitability associated with the treatment of the former (March 2004, by U.S. Food and Drug Administration ("FDA"), *Innovation/Stagnation: Challenge and Opportunity on the Critical Path to New Medical Products*; and December 2003, by Sellers, L. J., "Big Pharma bails on anti-infectives research", *Pharmaceutical Executive* 22). According to 10M and FDA, only two new classes of antibiotics have been developed in the past 30 years: oxazolidinones in 2000 and lipopeptides in 2003, and resistance to oxazolidinones have already been reported.

Gallium is a group IIIa semi-metallic element that has been used for many years for diagnosing neoplasms and inflammation in the field of nuclear medicine. Gallium has also shown some efficacy in the treatment of cancers (Adamson et al., 1975, *Cancer Chemothe. Rept* 59:599-610; Foster et al., 1986, *Cancer Treat Rep* 70:1311-1319; Chitambar et al., 1997, *Am J Clin Oncol* 20:173-178), symptomatic cancer-related hypercalcemia (Warrell et al., 1989, in "Gallium in the treatment of hypercalcemia and bone metastasis", *Important Advances in Oncology*, pp. 205-220, J. B. Lippincott, Philadelphia; Bockman et al., 1994, *Semin Arthritis Rheum* 23:268-269), bone resorption (Warrell et al., 1984, *J Clin Invest* 73:1487-1490; Warrell et al., 1989, supra), autoimmune diseases and allograft rejection (Matkovic et al., 1991, *Curr Ther Res* 50:255-267; Whitacre et al., 1992, *J Newuro immunol* 39:175-182; Orosz C. G. et al., 1996, *Transplantation* 61:783-791; Lobanoff M. C. et al., 1997, *Exp Eye Res* 65:797-801), stimulating wound healing and tissue repair (Bockman et al., U.S. Pat. No. 5,556,645; Bockman et al., U.S. Pat. No. 6,287,606) and certain infections, such as syphilis (Levaditi C. et al., 1931, *C R Hebd Seances Acad Sci Ser D Sci Nat* 192:1142-1143), intracellular bacterial, fungal or parasitic infections, such as tuberculosis, histoplasmosis, and leishmaniasis, respectively (Olakanmi et al., 1997, *J. Invest. Med.* 45:234 A; Schlesinger et al., U.S. Pat. No. 6,203,822; Bernstein, et al., International Patent Application Publication No. WO 03/053347), *Pseudomonas aeruginosa* infection (Schlesinger et al., U.S. Pat. No. 6,203,822), and trypanosomiasis (Levaditi C. et al. supra).

Although the exact mechanism of gallium's activity against bone resorption and hypercalcemia is not well known, its antiproliferative properties against cancer cells and antimicrobial activities are said to be likely due to its competition with ferric iron (i.e., $Fe^{3+}$) for uptake by cancer cells or microorganisms (Bernstein, 1998, Pharmacol Reviews 50(4): 665-682). Iron is an essential element for most living organisms, including many pathogens, and is required for DNA synthesis and various oxidation-reduction reactions (Byers et al., 1998, *Metal Ions Bio syst* 35:37-66; Guerinot et al., 1994, *Annu Rev Microbiol* 48:743-772; Howard, 1999, *Clin Micobiol Reviews* 12(3):394-404). $Ga^{3+}$ is known to have solution- and coordination-chemistries similar to those of $Fe^{3+}$ (Shannon, 1976, *Acta Crystallographica* A32:751-767; Huheey et al., 1993, In *Inorganic Chemistry: Principles of Structure and Reactivity I*, ed. 4, Harper Collins, NY; Hancock et al., 1980, *In Org Chem* 19:2709-2714) and behaves very similarly to $Fe^{3+}$ in vivo by binding to the iron-transport protein transferrin (Clausen et al., 1974, *Cancer Res* 34:1931-1937; Vallabhajosula et al., 1980, *J Nucl Med* 21:650-656). It is speculated that gallium enters microorganisms via their iron transport mechanisms and interferes with their DNA and protein synthesis.

U.S. Pat. No. 5,997,912 discloses a method for inhibiting growth of *Pseudomonas aeruginosa* by administering gallium compounds intravenously, orally or by aerosol and U.S. Patent Application Publication No. 2006/0018945 discloses a method of preventing or inhibiting biofilm growth formation using gallium compounds.

U.S. Pat. No. 6,203,822 and International Patent Application No. WO 03/053347 disclose methods for treating patients infected with intracellular bacteria, in particular, species of the genus *Mycobacterium*, by intravenously or orally administering gallium compounds to patients infected by this class of bacteria (also see Olakanmi et al., 2000, *Infection and Immunity* 68(10):5619-5627). These organisms primarily infect macrophages, which are known to store large amounts of iron and overexpress transferrin receptors. Parenterally or orally administered gallium compounds are readily taken up by macrophages through transferrin receptors and then, within these cells, are taken up by the infecting organisms, thereby interfering with the organisms' metabolism.

The antimicrobial activities of gallium against microorganisms other than intracellular organisms have thus far not been explored to a great extent.

Furthermore, the use of gallium compounds against the ever increasing number of multi-antibiotic resistant microorganisms has not been explored.

3. SUMMARY OF THE INVENTION

This invention is based upon the inventors' finding that gallium compounds are effective in controlling the growth of a variety of pathogenic, extracellular microorganisms, including those which are known to be resistant to conventional antibiotics and/or drugs.

Accordingly, the present invention provides methods for preventing and/or treating infectious diseases caused by extracellular microorganisms, said method comprising systemically administering to a subject in need thereof a prophylactically or therapeutically effective amount of a gallium compound. In a preferred embodiment, such extracellular microorganisms exclude *Pseudomonas aeruginosa* and *Legionella* spp., but include other iron-dependent, extracellular, pathogenic microorganisms. Such microorganisms may be bacteria or fungi, which infect host organisms, including mammals and birds, and most notably humans. Those microorganisms include, but are not limited to, bacteria within the genera, *Staphylococcus, Enterococcus, Escherichia, Streptococcus, Campylobacter, Salmonella, Helicobacter, Bacillus, Clostridium, Corynebacterium, Chlamydia, Coxilla, Ehrlichia, Francisella, Legionella, Pasteurella, Brucella, Proteus, Klebsiella, Enterobacter, Tropheryma, Acinetobacter, Aeromonas, Alcaligenes, Capnocytophaga, Erysipelothrix, Listeria, Yersinia*, and the like; and fungi, such as *Candida albicans, Microsporum canis, Sporothrix schenckii, Trichophyton rubrum, Trichophyton mentagrophytes, Malassezia furfur, Pityriasis versicolor, Exophiala werneckii, Trichosporon beigelii, Coccidioides immitis, Blastomyces dermatitidis, Aspergillus fumigatus, Epidermophyton* spp., *Fusarium* spp., *Zygomyces* spp., *Rhizopus* spp. *Mucor* spp., and so forth.

In another preferred embodiment, the microorganisms targeted by the present invention are resistant to at least one antibiotic or antimicrobial compound other than gallium compounds. In a specific embodiment, such drug-resistant microorganisms include, but are not limited to, methicillin-resistant *Staphylococcus aureus* (MRSA), vancomycin-resistant enterococci (VRE), ampicillin-resistant *E. coli* (e.g., *E. coli* O157:H7), fluoroquinolone-resistant *Salmonella typhi*, ceftazidime-resistant *Klebsiella pneumoniae*, and fluoroquinolone-resistant *Neisseria gonorrhoeae*, and the like.

In another aspect, the present invention provides a method for preventing and/or treating infectious diseases caused by extracellular microorganisms, other than *Pseudomonas aeruginosa* and *Legionella* spp., said method comprising systemically co-administering to a subject in need thereof a prophylactically or therapeutically effective amount of a gallium compound and at least one additional antimicrobial agent. Such additional antimicrobial agents include, but are not limited to, antibacterial agents, such as conventional antibiotics, antifungal agents, and other naturally or synthetically derived agents with antimicrobial activities.

3.1. Definitions

The term "subject" as used herein refers to an animal, including a fowl (e.g., chickens, turkeys, and the like), and a mammal such as a non-primate (e.g., cows, pigs, horses, cats, dogs, rats, etc.) and a primate (e.g., monkey and human), most preferably a human.

The term "systemic" or "systemically" as used herein refers to an administration of gallium compounds to a subject in a manner whereby the compound is distributed throughout the entire body of the subject mainly through the circulatory system, such as the cardiovascular system including the heart and blood vessels and the lymphatic system including lymph nodes, lymph vessels and ducts. Thus, systemic administrations of the gallium compound include oral administration and parenteral administration, including intravenous, intramuscular, subcutaneous, and intraperitoneal administrations, as well as suppositories, and the like. In certain situations, systemic administration can also provide an advantage of the direct contact of the compound with causative organisms, without going through the circulatory systems. For example, the gallium compound that is orally administered would exert its effect not only via systemic distribution but also via direct contact with the microorganisms that infect the digestive tracts.

The term "prophylactically effective amount" as used herein refers to that amount of the gallium compounds sufficient to prevent a disease or disorder associated with pathogenic microorganisms. A prophylactically effective amount can refer to the amount of the gallium compounds sufficient to prevent or suppress the growth of pathogenic microorganisms or kill pathogenic microorganisms in a subject.

The term "therapeutically effective amount" as used herein refers to that amount of the gallium compounds sufficient to treat, manage or ameliorate a disease or disorder caused by pathogenic organisms in a subject. A therapeutically effective amount can refer to the amount of the gallium compounds sufficient to reduce the number of pathogenic microorganisms, to suppress the growth of pathogenic microorganisms (i.e., stasis), or to kill pathogenic microorganisms at the affected sites or in the bloodstream of a subject. Further, a therapeutically effective amount of the gallium compounds means that the amount of the gallium compounds alone, or in combination with other therapies and/or other drugs, that provides a therapeutic benefit in the treatment, management, or amelioration of a disease or disorder.

4. DETAILED DESCRIPTION OF THE INVENTION

4.1. Iron Transport and Gallium

Most microorganisms, with a few exceptions (e.g., *Lactobacillus* spp.—see Archibald, 1983, *FEMS Microbiol Lett* 19:29-32; Weinberg, 1997, *Perspectives in Biology and Medicine* 40(4):578-583; and *Borrelia burgdorferi*—see Posey et al., 2000, *Science* 288:1651-1653), require iron for their survival (Weinberg, 1978, *Microbiol Rev* 42:45-66; Neilands, 1972, *Struct Bond* 11:145-170). Despite the fact that iron is one of the most abundant metals, its availability to microorganisms is limited due to its existence as insoluble compounds (oxides-hydroxides) in aerobic environments (Guerinot, 1994, supra; Spiro, et al., 1966, *J Am Chem Soc* 88:2721-2725; Vander Helm et al., 1994, In *Metal ions in fungi* vol. 11, pp. 39-98, Marcel Dekker, Inc. New York, N.Y.). Accordingly, microorganisms, such as bacteria and fungi, have developed various mechanisms for acquiring iron in the face of its limited availability in the environment (Howard, 1999, supra).

One such mechanism is the synthesis of potent iron-chelating compounds called siderophores. Microorganisms produce siderophores, which bind $Fe^{3+}$ in the environment and are transported into the cells of the microorganisms via specific transport systems, where $Fe^{3+}$ is released as $Fe^{2+}$ and then stored. Known siderophores include hydroxamates, such as rhodotorulic acid, coprogens, ferrichromes, and fusarinines; polycarboxylates; phenolates-catecholates and desferioxamine (Howard, 1999, supra). Other mechanisms include direct internalization of iron complexed with siderophores or host iron transporters (e.g., transferrin and lactoferrin), membrane-associated reductase mechanisms, and receptor-mediated mechanisms as well as membrane-mediated direct-transfer mechanisms (Howard, 1999, supra; Crosa, 1997, *Microbiol Mol Biol Rev* 61:319-336; Payne, 1994, *Methods Enzymol* 235:329-344). The availability of iron through these mechanisms is closely linked to the virulence of microorganisms (Litwin et al., 1993, *Clin Microbiol Reviews* 6(2):137-149), and each organism may have multiple alternative mechanisms for obtaining iron from iron-scarce environments to support its growth and survival (for example, see Spatafora et al., 2001, *Microbiology* 147:1599-1610).

It has been reported that gallium ion ($Ga^{3+}$) and ferric ion ($Fe^{3+}$) have strong biochemical similarities, in particular, with regard to their binding to proteins and chelators. These similarities are mainly attributed to their comparable ionic radii and the degrees of ionic (electrostatic) versus covalent contributions to bonding (for review, see Bernstein, 1998, supra). Because of these similarities, $Ga^{3+}$ can mimic $Fe^{3+}$ in various biological processes. For example, $Ga^{3+}$ binds to transferrin (see, for example, Clausen et al., 1974, *Cancer Res* 34:1931-1937; Vallabhajosula et al., 1980, *J Nucl Med* 21:650-656) and is transported into the cell via transferrin-mediated endocytosis (Chitambar, 1987, *Cancer Res* 47:3929-3934).

Without intending to be bound by theory, it is believed that $Ga^{3+}$ can competitively bind to siderophores and be easily taken up by microorganisms, where it can disrupt DNA and protein syntheses or bind to bacterial proteins and impair the growth of the microorganisms, thereby eventually leading to the stasis or death of the organisms. Alternatively, it is possible that $Ga^{3+}$ may occupy membrane-reductases of the microorganisms and prevent $Fe^{3+}$ from binding to the reductases to be reduced to $Fe^{2+}$, which would be more bioavailable than $Fe^{3+}$. Since the uptake of gallium does not immediately kill the microorganisms but rather leads to an initial stasis (i.e., a state where the growth or multiplication of microorganisms is inhibited), it has a reduced risk for generating resistant microorganisms. Furthermore, because iron is an essential element for pathogenic microorganisms for their survival and the biochemical similarities between iron and gallium are so close, it is additionally less likely for the microorganisms to be able to develop mechanisms that can discriminate iron from gallium and become resistant to gallium. Gallium may also prevent a microorganism from producing toxins by interfering with its toxin enzyme production.

The present invention takes advantage of these characteristics of gallium compounds and provides methods for preventing or treating infectious diseases caused by such pathogens, including those that are resistant to at least one antimicrobial agent other than gallium.

4.2. Gallium Compounds

Gallium compounds suitable for use in the present invention include any gallium-containing compounds that are pharmaceutically acceptable and safe for animal use, such as avian and mammalian use, in particular, for human use. Gallium compounds have been used diagnostically and therapeutically in humans and are known to be safe for human use (see Foster et al., 1986, supra; Todd et al., 1991, *Drugs* 42:261-273; Johnkoff et al., 1993, *Br J Cancer* 67:693-700).

Pharmaceutically acceptable gallium compounds suitable for use in the present invention include, but not by way of limitation, gallium nitrate, gallium maltolate, gallium citrate, gallium phosphate, gallium chloride, gallium fluoride, gallium carbonate, gallium formate, gallium acetate, gallium sulfate, gallium tartrate, gallium oxalate, gallium oxide, and any other gallium compounds which can safely provide effective levels of element gallium in various applications. Furthermore, gallium complexes, such as gallium pyrones, gallium pyridones, and gallium oximes, as well as gallium bound to proteins, such as transferrin and lactoferrin, or gallium bound to siderophores, such as hydroxamates, polycarboxylates, and phenolates-catecholates, desferioxamine and other iron-chelators, such as cysteine, α-keto acids, hydroxy acids and pyridoxal isonicotinyl hydrazone class (Richardson et al., 1997, *Antimicrobial Agents and Chemotherapy* 41(9):2061-2063) and the like are also suitable for use in the present invention.

4.3. Pharmaceutical Use of Gallium Compounds

The present invention is directed to methods for preventing or treating infectious diseases by systemically administering to a subject in need thereof a prophylactically or therapeutically effective amount of gallium compounds.

Examples of infectious diseases treatable by the present invention are those as to which the subject to be treated can benefit from a systemic administration of gallium compounds and include, but are not limited to, those caused by extracellular bacteria of the species of *Staphylococcus*, such as *Staphylococcus aureus, Staphylococcus epidermidis*, and the like; of *Enterococcus*, such as *Enterococcus faecalis, Enterococcus faecium*, and the like; of *Salmonella*, such as *Salmonella typhi, Salmonella typhimurium, Salmonella enterica*, and the like; of *Escherichia*, such as *Escherichia coli*, and the like; of *Streptococcus*, such as *Streptococcus pneumoniae*, *Streptococcus pyogenes*, *Streptococcus agalactiae*, and the like; of *Helicobacter*, such as *Helicobacter pylori*, and the like; of *Campylobacter*, such as *Campylobacter jejuni*, and the like; as well as the species of genera, *Yersinia, Chlamydia, Coxilla, Ehrlichia, Francisella, Legionella, Pasteurella, Brucella, Proteus, Klebsiella, Enterobacter, Tropheryma, Acinetobacter, Aeromonas, Alcaligenes, Capnocytophaga, Bacillus, Clostridium, Corynebacterium, Erysipelothrix, Listeria* and the like. Examples of infectious diseases treatable by the present invention also include infections caused by fungi, such as *Candida albicans, Microsporum canis, Sporothrix schenckii, Trichophyton rubrum, Trichophyton mentagrophytes, Malassezia furfur, Pityriasis versicolor, Exophiala werneckii, Trichosporon beigelii, Coccidioides immitis, Blastomyces dermatitidis, Aspergillus fumigatus, Epidermophyton* spp., *Fusarium* spp., *Zygomyces* spp., *Rhizopus* spp. *Mucor* spp., and so forth.

Gallium compounds can be administered by any methods that result in systemic distribution or delivery of the gallium compounds and include oral administration and parenteral administration, such as intravenous administration, intramuscular administration, subcutaneous administration, intraperitoneal administration, and the like. In certain infections, oral administration of gallium compounds provides not only systemic distribution/delivery of the gallium compounds to the affected area but also a direct contact of the compounds with the causative microorganisms in the affected area, such as within the digestive tracts. Thus, oral administration of the gallium compounds is especially useful in preventing or treating digestive tract infections caused by various microorganisms, including, but not limited to, *Staphylococcus aureus, Enterococcus faecalis, Enterococcus faecium, Salmonella typhi, Salmonella typhimurium, Salmonella enterica, Escherichia coli, Campylobacter jejuni, Clostridium difficile, Clostridium perfringens*, and the like. *Helicobacter pylori* that causes gastric and duodenal ulcers, gastritis, duodenitis, and gastric cancer, is also a good target for the methods of the present invention.

Furthermore, the methods of the present invention can be applied to preventing or treating infectious diseases caused by microorganisms that are resistant to at least one antimicrobial agent other than gallium compounds. The term "antimicrobial agent" used herein refers to any naturally or synthetically derived agent that kills microorganisms or inhibits the growth thereof, directly or indirectly, and includes conventional antibiotics as well as synthetic chemotherapeutic agents, such as sulfonamides, isoniazid, ethambutol, AZT, synthetic peptide antibiotics, and the like. Thus, in a specific embodiment, the infectious diseases preventable or treatable by the present invention are caused by antimicrobial-resistant strains of microorganisms mentioned above, in particular, of *Staphylococcus aureus, Enterococcus faecium, Enterococcus faecalis, E. coli, Salmonella typhi, Campylobacter jejuni, Klebsiella pneumoniae, Neisseria gonorrhoeae, Candida albicans*, and the like. More specifically, such antimicrobial-resistant organisms include methicillin-resistant *Staphylococcus aureus* (MRSA), vancomycin-resistant enterococci (VRE), ampicillin-resistant *E. coli* (e.g., *E. coli* O157:H7), fluoroquinolone-resistant *Salmonella thyphi*, ceftazidime-resistant *Klebsiella pneumoniae*, fluoroquinolone-resistant *Neisseria gonorrhoeae*, and the like. The methods of the present invention can be applied to any other pathogenic microorganisms which have become resistant to antimicrobial agents other than gallium, as far as they are dependent on iron for their growth and survival.

Gallium compounds to be used in the present invention can be formulated in conventional manner using one or more pharmaceutically acceptable carriers or excipients. As used herein the phrase "pharmaceutically acceptable carriers or excipients" is intended to include any and all solvents, dispersion media, coatings, isotonic and absorption delaying agents, and the like, which are compatible with pharmaceutical administration. The use of various pharmaceutically acceptable carriers or excipients for pharmaceutically active substances is well known in the art. With regard to gallium compounds, an injectable formula of gallium nitrate (Ganite™) is commercially available from Genta Inc (Berkeley Heights, N.J.). Ganite™ is an aqueous solution of $Ga(NO_3)$. $9H_2O$ and sodium citrate dehydrate. An oral formula of gallium maltolate developed by Titan Pharmaceuticals, Inc. (San Francisco, Calif.) is currently in Phase II clinical testing in patients with metastatic prostate cancer and refractory multiple myeloma.

The therapeutically effective amount (i.e., dosage) of a gallium compound can vary based on the nature and severity of the infection to be treated, the types of etiologic microorganism, the location of the affected area, the method of administration, the age and immunological background of a subject, the types of gallium compound used, as well as other factors apparent to those skilled in the art. Typically, a therapeutically effective amount of a gallium compound can be that amount which gives a gallium concentration at the affected area of the body or in blood plasma, of at least about 1 µM, at least about 50 µM, at least about 100 µM, at least about 500 µM, at least about 1 mM, at least about 10 mM, at least about 50 mM, at least about 100 mM, at least about 200 mM, up to about 500 mM. Due to gallium's low toxicity, the amount may be liberally increased to more than 500 mM but less than that amount which causes any toxicity. For reference, it has been reported that healthy adults can tolerate at least about 200 mg/m²/day gallium nitrate intravenous infusion for at least 7 days (see U.S. Pat. No. 6,203,822, supra). Also, an oral administration of 100 mg to 1400 mg per 24 hours as a single agent did not cause major toxicity in ovarian cancer patients and lung cancer patients (see Collery et al., 2002, "Gallium in cancer treatment", *Oncology/Hematology* 42:283-296). Thus, for the methods of the present invention, what is contemplated is administration of the gallium compounds at dosages of, at least about 10 mg/m²/day, at least about 50 mg/m²/day, at least about 100 mg/m²/day, at least about 200 mg/m²/day, at least about 300 mg/m²/day, at least about 500 mg/m²/day, at least about 600 mg/m²/day, at least about 700 mg/m²/day, or at least about 800 mg/m²/day, but less than that dosage which causes any toxicity.

The prophylactically effective amount of a gallium compound may be that amount sufficient to prevent a disease or disorder associated with pathogenic microorganisms and may vary based on the location of the affected area, the types and the number of the pathogenic organisms in the area, the types of gallium compound to be used, as well as on the methods of application and other factors apparent to those skilled in the art. Typically, the prophylactically effective amount of a gallium compound may be that amount which gives a gallium concentration at the affected area of the body or in blood plasma, of at least about 0.1 µM, at least about 50 µM, at least about 100 µM, at least about 500 µM, at least about 1 mM, at least about 10 mM, at least about 50 mM, at least about 100 mM, up to about 200 mM. Again, the amount of a gallium compound for prophylactic purposes may be liberally increased to more than 200 mM but less than the amount that causes any toxicity.

In another aspect, the present invention provides a method for preventing and/or treating infectious diseases caused by extracellular microorganisms, said method comprising co-administering to a subject in need thereof prophylactically or therapeutically effective amounts, individually or collectively, of a gallium compound and at least one additional antimicrobial agent. The term "co-administration" or "co-administering" used herein refers to the administration of gallium compound and at least one additional antimicrobial agent either sequentially in any order or simultaneously, by the same administration method or a combination of different administration methods, for example, by an intravenous administration of the gallium compound and an oral administration of the additional antimicrobial agent, or vice versa. Such co-administration of one or more additional antimicrobial agents together with the gallium compound is especially beneficial because the drugs attack the causative organisms by non-overlapping, completely different mechanisms, and/or because the development of antimicrobial resistance in the organisms may involve different mechanisms for the different antimicrobial agents, thereby causing nearly complete eradication of the organisms, by the drugs themselves or in combination with the actions by the host's own immune system and reducing or eliminating the chance for the causative organisms to develop resistance to the drugs. Furthermore, thanks to the low toxicity of gallium, by increasing the dosage of gallium, a combination therapy can reduce the dosage of an additional antimicrobial agent to an amount less than that required when the latter is used alone, thereby reducing adverse effects of the latter. Moreover, co-administration of a gallium compound and an additional antimicrobial agent may result in a synergistic effect and, thus, require less dosages than those required when each is used alone.

Additional antimicrobial agents that can be co-administered with gallium compounds can be antibacterial agents or antifungal agents, depending on the type of the causative organisms. Examples of antibacterial agents include, but not by way of limitation, those in the classes of penicillins, including amipicillin, flucloxacillin, dicloxacillin, methicillin, ticarcillin, piperacillin, carbapenems, mecillinams, and the like; cephems, including cephalosporin and cephamycins; sulfonamides; aminoglycosides, including amikacin, gentamicin, kanamycin, neomycin, netilmicin, paromomycin, streptomycin, tobramycin, apramycin, and the like; chloramphenicol; tetracyclines, including chlortetracycline, oxytetracycline, demeclocycline, doxycycline, lymecycline, meclocycline, methacycline, minocycline, rolitetracycline, and the like; macrolides, including erythromycin, azithromycin, clarithromycin, dirithromycin, roxithromycin, carbomycin A, josamycin, iktasamycin, oleandomycin, spiramycin, troleandomycin, tylosin/tylocine, telithromycin, cethromycin, ansamycin, and the like; lincosamides, including lincomycin, clindamycin, and the like; streptogramins, including mikamycins, pristinamycins, oestreomycins, virginiamycins, and the like; glycopeptides, including acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin, and the like; rifamycins, including rifampicin, rifabutin, rifapentine, and the like; nitroimidazoles, including metronidazole, nitrothiazoles, and the like; quinolones, including nalidixic acid, cinoxacin, flumequine, oxolinic acid, piromidic acid, pipemidic acid, ciprofloxacin, enoxacin, fleroxacin, lomefloxacin, nadifloxacin, norfloxacin, ofloxacin, pefloxacin rufloxacin, balofloxacin, grepafloxacin, levofloxacin, pazufloxacin mesilate, sparfloxacin, temafloxacin, tosufloxacin, clinafloxacin, gemifloxacin, moxifloxacin, gatifloxacin, sitafloxacin, trovafloxacin, and the like; dihydrofolate reductase inhibitors, including trimethoprim; oxazolidinones, including linezolid, eperezolid, and the like; lipopeptides, including gramicidins, polymyxins, surfactin, and the like; and analogs, salts and derivatives thereof. Examples of antifungal agents include, but are not limited to, polyenes, such as amphotericin, nystatin, pimaricin, and the like; azole drugs, such as fluconazole, itraconazole, ketoco, and the like; allylamine and morpholine drugs, such as naftifine, terbinafine, amorolfine, and the like; antimetabolite antifungal drugs, such as 5-fluorocytosine, and the like; and analogs, salts and derivatives thereof.

Which antimicrobial agent should be used in combination with the gallium compounds in any given infection can be determined by various simple and routine methods known to one skilled in the art. For example, an infectious microorganism isolated from a patient can be tested for its sensitivity to various antimicrobial agents using a standardized disk-diffusion method (e.g., Kirby-Bauer disk-diffusion method). Briefly, in this method, an appropriate agar plate is uniformly inoculated with the test organism and paper disks impregnated with predetermined concentrations of different antibiotics are placed on the agar surface. After incubation, the diameter of a circular zone, around the disks, in which the growth of the organism is inhibited is measured. The diameter of the inhibition zone is a function of the amount of the antibiotic in the disk as well as the susceptibility of the organism to the antibiotic. The antibiotics to which the organism shows susceptibility can be used for a combination treatment with the gallium compounds. Other examples of antibiotic susceptibility tests include, but are not limited to, a broth tube dilution method for determining Minimum Inhibitory Concentration (MIC) and Minimum Bactericidal Concentration (MBC) of a given antimicrobial agent against a given organism. These methods are described in Section 6.1, infra.

Thus, in a specific embodiment, an infection caused by MRSA can be treated by co-administration of gallium compound and vancomycin or linezolid (e.g., ZyVox™ by Pfizer, NY) to a subject in need thereof. Vancomycin and Zyvox™, respectively, are currently used as the antibiotics of choice to treat MRSA infections. Likewise, in another specific embodiment, an infection caused by VRE can be treated by co-administration of a gallium compound and linezolid. In yet another specific embodiment, an infection or a disease/disorder (e.g., peptic ulcers, gastritis, duodenitis, gastric cancer, and the like) caused by *Helicobacter pylori* can be treated by co-administration of a gallium compound and clarithromycin, amoxicillin and/or metronidazole. Other agents that directly or indirectly inhibit or suppress the growth of *Helicobacter pylori* can be also co-administered with the gallium compound. Such agents include, but are not limited to, proton pump inhibitors, such as omeprazole that is currently used together with clarithromycin and amoxicillin in triple therapy for peptic ulcers; and urease inhibitors, such as fluorofamide, acetohydroxamic acid, certain divalent metal ions, including Zn, Cu, Co, and Mn, and the like; as well as other agents, such as bismuth compounds (e.g., bismuth subsalicylate) that not only protect the stomach lining by coating the latter, but also suppress *H. pylori* growth (S. Wagner et al., 1992, "Bismuth subsalicylate in the treatment of H2 blocker resistant duodenal ulcers: role of *Helicobacter pylori*", Gut 33:179-183).

In another aspect, the present invention provides a kit comprising one or more vials containing a gallium compound and one or more additional antimicrobial agents.

5. EXAMPLES

The following examples are provided to further illustrate the current invention but are not intended to in any way limit the scope of the current invention.

5.1. In Vitro Study

Susceptibility of Microorganisms to Gallium

Example 1

Susceptibility of various microorganisms to gallium was tested by determining the minimum inhibitory concentration (MIC) and minimum bactericidal concentration (MBC) for each microorganism using gallium nitrate. In general, MIC is determined by (i) mixing a series of broths, each containing a standard number of microorganisms, with serially diluted solutions of the gallium compound; and (ii) determining the MIC, after incubation, that is the lowest concentration of the gallium compound that inhibits the growth of the microorganism. The lower the MIC, the more susceptible the organism is. The MBC is determined by subculturing an aliquot of each sample from the MIC test on an appropriate agar plate containing no gallium compound. After incubation, the MBC is determined to be the lowest concentration of the gallium compound at which no growth is observed.

Specifically, in the present experiment, two grams of gallium nitrate powder were dissolved in 10 ml of filter-sterilized deionized water and the resulting 20% (w/v) (i.e., 200 mg/ml) solution was once again filter-sterilized. Two-fold serial dilutions were prepared in sterile deionized water down to 0.156% (i.e., 1.56 mg/ml) for the tests for most of the organisms, except for the test for *Candida albicans*, in which 10%, 1%, 0.5%, 0.1%, 0.05%, 0.01%, 0.005% and 0.001% of gallium nitrate solutions were prepared.

Table 1 shows the list of microorganisms tested for MIC and MBC. All organisms were obtained from the American Type Culture Collection (ATCC), Manassas, Va. Each microorganism was picked from the seed culture (see Table 1) and inoculated in an appropriate type of broth to obtain a 0.5 McFarland turbidity standard. The standard suspension of the microorganism was then diluted to 1:100 with the broth and used for the tests.

TABLE 1

| TEST ORGANISM | ATCC # | SEED CULTURE |
|---|---|---|
| *Candida albicans* | 10231 | On Sabouraud dextrose agar, at 25-30° C. for 24-48 hours. |
| Methicillin-resistant *Staphylococcus aureus* (MRSA)[a] | 33592 | On tryptic soy agar with 5% sheep blood (BAP), at 35-37° C. for 24-48 hours under aerobic conditions. |
| Vancomycin-resistant *Enterococcus faecalis* (VRE)[b] | 51575 | |
| *Escherichia coli* O157:H7 | 35150 | |
| *Salmonella typhi* | 6539 | |
| *Campylobacter jejuni* | 29428 | On *Brucella* agar with 5% sheep blood, at 35-37° C. for 48 hours under microaerophilic conditions (CampyPak ™ by BBL Microbiology Systems, Cockeysville, Md). |

[a]Antibiotics resistance of the organism was confirmed by CLSI (Clinical Laboratory Standards Institute) Oxacillin disk-diffusion test. The zone of inhibition was 6 mm (CLSI Oxacillin resistant range: ≤10 mm).
[b]Antibiotics resistance of the organism was confirmed by CLSI Vancomycin disk-diffusion test. The zone of inhibition was 10 mm (CLSI Vancomycin resistant range: ≤14 mm).

Each microorganism was tested in duplicate by either a microdilution broth method in 96-well plates (i.e., 0.1 ml of the gallium nitrate solution mixed with 0.1 ml of the microorganism suspension) or a macrodilution broth method in test tubes (i.e., 1 ml of the gallium nitrate solution mixed with 1 ml of the microorganism suspension) as follows:

Microdilution broth method: *Candida albicans*; *Escherichia coli* O157:H7; and *Campylobacter jejuni*.

Macrodilution broth method: Methicillin-resistant *Staphylococcus aureus* (MRSA); Vancomycin-resistant *Enterococcus faecalis* (VRE); and *Salmonella typhi*.

The growth of the microorganisms were determined by visual observation of turbidity in the samples.

The following controls were incubated together with the test samples:

Viability control: A mixture of equal volumes of deionized water and an appropriate broth inoculated with a test microorganism but without gallium nitrate; and Sterility control: A mixture of equal volumes of deionized water and an appropriate broth without either microorganisms or gallium nitrate.

Purity of each microorganism was confirmed by streaking an appropriately diluted suspension of the microorganism onto an appropriate agar plate to obtain isolated colonies and observing colony morphology.

The concentrations of microorganisms in the suspension used in MIC test were determined by inoculating serial dilutions of the suspensions onto appropriate agar plates and counting the number of colonies.

To determine MBC, 10 µl of each sample used in MIC were inoculated onto an appropriate agar plate and incubated. The lowest concentration of the gallium nitrate that showed no growth was determined to be the MBC.

The results are shown in Table 2 below.

TABLE 2

| Test Organism | Broth (MIC) | Agar Plate (MBC) | Incubation Condition | Final Concentration of Organism (CFU/ml) | MIC (mg/ml) | MBC (mg/ml) |
|---|---|---|---|---|---|---|
| *Candida albicans* | Sabouraud Dextrose | Sabouraud dextrose agar | At 27° C. for 48 hours | $9.75 \times 10^5$ | 10 | >100 |
| *Staphylococcus aureus* (MRSA) | Muller Hinton | Tryptic soy agar with 5% sheep blood | At 36° C. for 48 hours | $5.2 \times 10^5$ | ND | 12.5 |
| *Enterococcus faecalis* (VRE) | Muller Hinton | Tryptic soy agar with 5% sheep blood | At 36° C. for 48 hours | $3.9 \times 10^5$ | ND | 25 |
| *Escherichia coli* O157:H7 | Muller Hinton | Tryptic soy agar with 5% sheep blood | At 36° C. for 48 hours | $1.38 \times 10^6$ | ND | 6.25 |

TABLE 2-continued

| Test Organism | Broth (MIC) | Agar Plate (MBC) | Incubation Condition | Final Concentration of Organism (CFU/ml) | MIC (mg/ml) | MBC (mg/ml) |
|---|---|---|---|---|---|---|
| Salmonella typhi | Muller Hinton | Tryptic soy agar with 5% sheep blood | At 36° C. for 48 hours | $8.3 \times 10^5$ | ND | 6.25 |
| Campylobacter jejuni | Muller Hinton | Tryptic soy agar with 5% sheep blood | At 36° C. for 48 hours | $4.9 \times 10^5$ | ND | <0.78 |

* ND: Not determined due to non-specific turbidity caused by the precipitation of gallium nitrate at some dilutions.

5.2. In Vivo Study

Effect of Gallium Nitrate in Animal Models

Example 2

Methicillin-Resistant *Staphylococcus aureus* (MRSA)

Adult BALBc mice are inoculated with $1 \times 10^6$ CFU/mouse of *Staphylococcus aureus*-MRSA strain (e.g., ATCC 33592) by intraperitoneal injection. Following bacterial injections (approximately 8 hours post-inoculation), each mouse receives a single intravenous injection of one of the following: 0.9% saline (control), 30 mg/kg, 45 mg/kg, or 60 mg/kg of gallium nitrate, 200 mg/kg of vancomycin, or 45 mg/kg of gallium nitrate and 200 mg/kg of vancomycin, all in 0.9% saline. Initially, there are 5 mice in each of the six groups. Following inoculation, the mice are monitored twice daily for morbidity. Body temperature is obtained twice daily and a mouse whose body temperature decreases by 4° C. or greater will be considered moribund and euthanized. Body weights are taken once daily for the duration of the study. On Day 5, all remaining animals are euthanized. Spleen, lymph nodes and kidneys are collected, homogenized in sterile PBS and serially diluted for bacterial quantitation.

Example 3

Vancomycin-Resistant *Enterococcus faecalis* (VRE)

Adult CF1 mice are caged individually and total counts of native enterococci and possible VRE in colony forming unit (CFU) per gram of feces are determined as a baseline for each mouse. On Day 1, each mouse receives 0.5 ml (about $10^9$ CFU/ml) of VRE (e.g., ATCC 51575) suspension in Muller-Hinton broth (MHB), or MHB alone (control), via gavage with a stainless steel feeding tube. At specified intervals thereafter (e.g., 1, 7, 14 days and so on), 2 fresh fecal pellets from each mouse are collected, weighed, and emulsified in MHB and the numbers of CFU of VRE, enterococci, and gram-negative enteric bacilli per gram of feces are determined by standard serial dilution and plating techniques. For example, total enterococcal counts can be measured with bile-esculin agar, counts of enteric bacilli with MacConkey agar, and counts of VRE with Muller-Hinton II agar containing vancomycin (50 µg/ml), streptomycin (100 µg/ml), polymyxin (100 µg/ml) and nystatin (2 µg/ml) (see M. S. Whitman et al., 1996, "Gastrointestinal tract colonization with vancomycin-resistant *Enterococcus faecium* in an animal model", Antimicrobial Agents and Chemotherapy 40(6):1526-1530). Groups of mice (at least 5 mice/group) are assigned to receive daily either sterile drinking water (control), or drinking water containing 100 µg/ml, 200 µg/ml or 300 µg/ml of gallium citrate, 250 µg/ml of vancomycin, 250 µg/ml of linezolid, or 200 µg/ml of gallium citrate and 250 µg/ml of linezolid, starting 24 hours after the inoculation of the mice up to 10 days. Counts of VRE and total enterococci in feces are determined for each group at specified intervals up until 40 days after the inoculation and compared with the baseline counts.

Example 4

*Helicobacter pylori*

C57BL/6 mice are inoculated with the mouse-adapted *Helicobacter pylori* SS1 strain (Lee A, O'Rouke et al., 1997, "A standardized mouse model of *Helicobacter pylori* infection: introducing Sydney strain", Gastroenterology 112:1386-97) by intragastric delivery of 0.1 ml of the bacterial suspension (approximately $1-2 \times 10^9$ bacteria/ml) in an appropriate medium (e.g., *brucella* broth). Control mice are given 0.1 ml of the medium without the bacteria. Mice are left for 1-3 weeks for bacterial colonization to become established. Groups of mice (at least 5 mice/group) are assigned to receive daily, via intragastric gavage, either sterile saline (control), or 60 mg/kg, 80 mg/kg or 100 mg/kg of gallium maltolate with or without 15 mg/kg of omeprazole in saline solution for 14 days. Mice are euthanized 24 hours after the completion of the treatment. A longitudinal section of gastric tissue is removed, fixed in formalin solution, embedded in paraffin and cut at 8µ to produce histologic sections. The sections are prepared with Giemsa stain and examined microscopically for *Helicobacter pylori* colonization of the gastric mucosa. A second longitudinal section of gastric tissue is removed, weighed and homogenized in 1 ml *brucella* broth. The homogenate is diluted in phosphate-buffered saline and an aliquot is plated, in duplicate, on a selective medium (e.g., blood agar supplemented with 5% defibrinated sheep blood, 100 µg/ml vancomycin, 3.3 µg/ml polymixin B, 200 g/ml bacitracin, 10.7 µg/ml nalidixic acid and 50 µg/ml amphotericin B (see J. I. Keena et al., 2004, "The effect of *Helicobacter pylori* infection and dietary iron deficiency on host iron homeostasis: A study in mice", *Helicobacter* 9(6):643-650). Growth of *Helicobacter pylori* is confirmed based on Gram staining, morphology and urease production. The numbers of colony forming unit (CFU) per gram of tissue are determined and compared among the groups.

6. EQUIVALENTS

Those skilled in the art to which the present invention is related will recognize, or be able to ascertain, many equivalents to the specific embodiments of the invention described herein using no more than routine experimentation. Such equivalents are intended to be encompassed by the following claims.

All publications, patents and published patent applications mentioned in this specification are herein incorporated by reference into the specification.

Citation or discussion of a reference herein shall not be construed as an admission that such is prior art to the present invention.

The invention claimed is:

1. A method for treating an infectious disease caused by methicillin-resistant *Staphylococcus aureus* ("MRSA"), said method comprising intravenously administering to a subject in need thereof a therapeutically effective amount of gallium maltolate, said MRSA being present in the bloodstream of said subject, wherein said therapeutically effective amount is sufficient to reduce the number of said MRSA in the bloodstream of said subject, to suppress the growth of said MRSA in the bloodstream of said subject, or to kill said MRSA in the bloodstream of said subject.

2. The method of claim 1, further comprising co-administering a therapeutically effective amount of at least one additional antimicrobial agent.

3. A method for treating an infectious disease caused by methicillin-resistant *Staphylococcus aureus* ("MRSA"), comprising co-administering to a subject in need thereof therapeutically effective amounts, individually or collectively, of gallium maltolate, and at least one additional antimicrobial agent, said MRSA being present in the bloodstream of said subject, wherein said gallium maltolate is administered intravenously, and wherein said therapeutically effective amount is sufficient to reduce the number of said MRSA in the bloodstream of said subject, to suppress the growth of said MRSA in the bloodstream of said subject or to kill said MRSA in the bloodstream of said subject.

4. The method of claim 3, wherein said additional antimicrobial agent is vancomycin and/or linezolid.

5. A method for treating an infection in the bloodstream of a subject, said infection being by a methicillin-resistant *Staphylococcus aureus* ("MRSA"), said method comprising intravenously administering to a subject in need thereof a therapeutically effective amount of gallium maltolate, wherein said therapeutically effective amount is sufficient to reduce the number of said MRSA in the bloodstream of said subject, to suppress the growth of said MRSA in the bloodstream of said subject, or to kill said MRSA in the bloodstream of said subject.

* * * * *